US 8,613,699 B2

(12) United States Patent
Irion et al.

(10) Patent No.: US 8,613,699 B2
(45) Date of Patent: Dec. 24, 2013

(54) DEVICE FOR THE STERILE SHEATHING OF A STERILIZATION-SENSITIVE OPERATING PART

(75) Inventors: Klaus M. Irion, Emmingen-Liptingen (DE); Christian Graf, Emmingen-Liptingen (DE); Peter Schwarz, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 750 days.

(21) Appl. No.: 12/130,760

(22) Filed: May 30, 2008

(65) Prior Publication Data

US 2008/0300553 A1 Dec. 4, 2008

(30) Foreign Application Priority Data

May 31, 2007 (DE) .......................... 10 2007 026 235

(51) Int. Cl.
*A61B 1/00* (2006.01)
(52) U.S. Cl.
USPC ........................................................ 600/122
(58) Field of Classification Search
USPC ......... 604/533, 534, 535, 536, 121, 263, 110; 600/122
See application file for complete search history.

(56) References Cited

U.S. PATENT DOCUMENTS

| | | | |
|---|---|---|---|
| 4,911,148 A * | 3/1990 | Sosnowski et al. ........... | 600/136 |
| 5,078,483 A | 1/1992 | Herzberg | |
| 5,269,761 A * | 12/1993 | Stehrenberger et al. ...... | 604/110 |
| 5,301,657 A | 4/1994 | Lafferty et al. | |
| 5,562,602 A * | 10/1996 | Yabe et al. .................... | 600/121 |
| 6,416,462 B1 | 7/2002 | Tovey et al. | |
| 6,908,428 B2 * | 6/2005 | Aizenfeld et al. ............ | 600/123 |

FOREIGN PATENT DOCUMENTS

| | | |
|---|---|---|
| DE | 8812027 U1 | 11/1988 |
| DE | 3920508 A1 | 1/1991 |
| DE | 60017242 T2 | 12/2005 |
| DE | 202007014102 U1 | 2/2008 |
| EP | 0904016 B1 | 11/2004 |
| WO | 9204932 | 4/1992 |
| WO | 2007057881 A2 | 5/2007 |

OTHER PUBLICATIONS

European Search Report; EP 08 00 9824; Feb. 11, 2010; 1 page.

* cited by examiner

*Primary Examiner* — Kevin C Sirmons
*Assistant Examiner* — Brandy S Lee
(74) *Attorney, Agent, or Firm* — St. Onge Steward Johnston & Reens LLC

(57) ABSTRACT

A device for the sterile sheathing of a sterilization-sensitive operating part, which can be connected to a medical instrument for surgical intervention, having a handling element, which comprises a bundled sterile hose at a distal end, whereby the handling element further comprises an opening, through which the sterilization-sensitive operating part can be inserted from proximal to distal into the sterile hose such that the sterilization-sensitive operating part can thereby be sheathed with the hose. It is suggested that a medical instrument is connected fixedly at its proximal end region to a distal end of the sterile hose, and that there is a transfer station, in which the sterilization-sensitive operating part is accommodated, whereby the handling element can be connected to the transfer station such that the medical instrument and the sterilization-sensitive operating part can be connected to one another and that this assembly can be withdrawn from the transfer station, whereby the bundled sterile hose can be pulled over the sterilization-sensitive operating part.

20 Claims, 4 Drawing Sheets

DEVICE FOR THE STERILE SHEATHING OF A STERILIZATION-SENSITIVE OPERATING PART

BACKGROUND OF THE INVENTION

The invention relates to a device for the sterile sheathing of a sterilization-sensitive operating part, which can be connected to a medical instrument for a surgical intervention, having a handling element, which comprises a bundled sterile hose at a distal end, whereby the handling element further comprises an opening, through which the sterilization-sensitive operating part can be inserted from proximal to distal into the sterile hose such that the sterilization-sensitive operating part can thereby be sheathed with the sterile hose.

Such a device for the sterile sheathing of a sterilization-sensitive operating part is known from DE 39 20 508 A1.

Such devices are employed for surgical interventions, in which devices are used which cannot be sterilized or only with difficulty.

Examples of such sterilization-sensitive operating parts include camera systems, used in connection with endoscopes for different surgical interventions.

An endoscopic camera system comprises a camera head, which comprises sensitive inner electronic components, e.g. a signal-processing unit, which processes the signals from an image-capture optical unit into video signals, suitable to be sent to a monitor.

Prior to a surgical intervention such a camera system is connected to a medical instrument, e.g. an endoscope. During the surgical intervention the surgeon can observe the operating site on a monitor. The surgeon manipulates assembly via an operating part of the camera system. The operating part can have still more control elements, such as switches, faucets, electric socket units etc., via which additional devices of the instrument, such as e.g. suction and rinsing lines, can be operated. Due to its complexity and sensitive components this operating part is sensitive to sterilization.

To avoid a sterilization of the camera system or respectively of the proximal handling part the camera system and its connection cable is sheathed in a sterile sheath in the form of a hose, before being mounted onto the endoscope. After the intervention the camera system is separated from the endoscope.

The device known from the abovementioned document comprises a handling element for this purpose in the form of a pick-up, to which a bundled sterile sheath is fixed. An operating part of a sterilization-sensitive camera is inserted through an opening in the pick-up into the pick-up to the extent where the camera is fixed in the pick-up. Then an outer protective cover, with which the pick-up is covered, is opened by a sterile person, and the camera is gripped through the sterile sheath by a hand of the surgeon and pulled away from the pick-up. As the camera is being taken out of the pick-up the camera and the camera cable are automatically sheathed in the sterile sheath.

Prior to the camera being taken out of the pick-up the camera can be connected to a medical instrument. The sterile sheath comprises an opening at its distal end for this purpose.

In order to connect the medical instrument to the sterilization-sensitive camera, which is fixed in the pick-up, a proximal end of the medical instrument is inserted through the distal opening in the sterile sheath into the interior of the sheath and connected there to a coupling element of the sterilization-sensitive camera.

Threading or respectively inserting the instrument through the narrow opening requires considerable concentration and certain dexterity. This normally requires both hands of a person, or one person holds the pick-up and the camera already inserted into the sheath and another person guides the instrument through the narrow opening into the sheath from the other side and attaches it to the camera. This procedure is laborious and unnecessarily prolongs preparation time for a surgical intervention. Furthermore contamination can enter the interior of the sterile sheath via the distal opening and thus reach the operating part of the camera actually to be protected.

It has also proven a disadvantage that when the camera is removed from the pick-up a sterile person must grip the camera through the hose-like sheath. The sheath can thereby also be damaged resulting in the sterilization-sensitive camera being contaminated anyhow.

One object of the invention is therefore to further develop a device for the sterile sheathing of a sterilization-sensitive operating part of the abovementioned type to the effect that connecting the medical instrument to the sterilization-sensitive operating part and sheathing the sterilization-sensitive operating part can be done easily by one person, one-handed if possible, without any danger of a contamination of the sterilization-sensitive operating part.

SUMMARY OF THE INVENTION

This object is achieved according to the invention by a medical instrument being connected fixedly at its proximal end region to a distal end of the hose, and by there being a transfer station, in which the sterilization-sensitive operating part is accommodated, whereby the handling element can be connected to the transfer station such that the medical instrument and the sterilization-sensitive operating part can be connected to one another, and by this assembly being able to be withdrawn from the transfer station, whereby the bundled hose can be pulled over the sterilization-sensitive operating part.

Fixedly connecting the medical instrument to the distal end of the sterile hose connected to the handling element firstly has the advantage that these three components can be prefabricated, assembled and sterilized as a compact sterile unit. Furthermore the prefabricated unit also has the considerable advantage that it takes only a single step to both connect the medical instrument to the sterilization-sensitive operating part, and place the sterile hose relative to the transfer station such that the sterilization-sensitive operating part is automatically sheathed with the hose when being withdrawn from the transfer station.

This step can be done using one (sterile) hand of a person from the sterile area, without the danger of the sterile area being contaminated or the hose being damaged. Using the other (not necessarily sterile) hand this person can prepare the transfer station beforehand.

In one work mode the sterilization-sensitive operating part is first fixed in the non-sterile area in the transfer station. In the sterile area the sterile unit consisting of handling element, hose and medical instrument is brought by a person to the transfer station using one hand and connected to the transfer station. At the same time the medical instrument is connected to the sterilization-sensitive operating part accommodated in the transfer station.

The sterile medical instrument can now be gripped by the surgeon. When the medical instrument is withdrawn from the transfer station the sterilization-sensitive operating part connected to the latter in the interim is withdrawn from the transfer station and automatically sheathed with the sterile hose.

The medical instrument can be designed in a number of configurations. It can be an endoscope having a purely observational function, and it can also additionally or exclusively be a tool, that is to say a working instrument. Examples of these are tools for tissue manipulation, such as drills or cutting elements. These can be driven by a motor. The drive or respectively the motor can be accommodated in the operating part.

In a further embodiment of the invention the handling element comprises a handle on the distal side.

The advantage of this measure is that the handle allows the docking procedure of the unit on the transfer station to be performed particularly safely and easily using one (sterile) hand.

In a further embodiment of the invention the handling element comprises a coupling on the proximal side.

The advantage of this measure is that the coupling, brought to the non-sterilized transfer station to connect the handling element to the transfer station, is spatially separated from the sterile area, in which both the handle and the sterile hose and the medical instrument fixedly connected to the hose are located. This further contributes to the sterile area being not contaminated.

In a further embodiment of the invention the handling element comprises a flat base part, from which the handle and the coupling protrude.

The advantage of this measure is that the flat base part separates the handle and the coupling from one another. This contributes to the surgeon not grasping the coupling by mistake. The base part prevents the hand gripping the handle from coming into contact with the transfer station.

In a further embodiment of the invention the sterile hose is fixed to the handle. The advantage of this measure is that the bundled hose can be affixed in a compact structural form.

In a further embodiment of the invention the handle is designed as an annular flange.

The advantage of this measure is that a handle designed in this way can be held securely by a surgeon. This ensures that the handling element with the sterile hose and the medical instrument do not fall out of the grasp of the surgeon when being attached to the transfer station.

In a further embodiment of the invention the coupling comprises a coupling element.

The advantage of this measure is that the handling element can be connected easily and specifically to the transfer station.

In a further embodiment of the invention the coupling is designed as a bayonet coupling.

The advantage of this measure is that the bayonet coupling can be designed structurally simple. The coupling element on the handling element can be designed as a pin, which can be contrived by an extremely simple procedure in terms of production technology. A bayonet guide on the transfer station can be contrived by a simple milling procedure.

In a further embodiment of the invention the base part of the handling element comprises an orientation feature.

The advantage of this measure is that through the provision of the orientation feature on the base part the surgeon can recognize particularly easily into which position the handling element must be brought for docking on the transfer station.

In a further embodiment of the invention the handling element and the hose are designed as disposable items.

The advantage of this measure is that after use the handling element and the hose do not have to be cleaned, but can simply be disposed of.

In a further embodiment of the invention the medical instrument is designed as a disposable instrument.

Here, too, there is again the advantage that after use the medical instrument does not have to be sterilized, but can be disposed of together with the handling element and the hose.

In a further embodiment of the invention, which can be used as an alternative to the abovementioned embodiment, the medical instrument is designed as a reusable instrument.

This measure is an advantage for expensive instruments. In this embodiment the medical instrument must be separated from the hose and the handling element after use and can be cleaned and sterilized to then be reconnected to the hose of a new handling element.

In a further embodiment of the invention the transfer station comprises a docking and undocking mechanism, which can be actuated via the handle.

The advantage of this measure is that the docking and undocking mechanism can be actuated from the sterile area. Actuating the docking and undocking mechanism can thus likewise be done one-handed by the same person who brought the assembly of the handling element and the medical instrument to the transfer station.

In a further embodiment of the invention, which can be used as an alternative to the abovementioned embodiment, the docking and undocking mechanism can be actuated via operational controls arranged on the transfer station.

In this embodiment operational controls, which are arranged on the non-sterilized transfer station, must be provided with a sterile cover prior to use. Actuating the docking and undocking mechanism using the operational controls can be done mechanically or electronically.

In a further embodiment of the invention the docking and undocking mechanism comprises a start position, in which the sterilization-sensitive operating part is locked in the transfer station.

The advantage of this measure is that the sterilization-sensitive operating part is locked in the transfer station against withdrawal, insertion and rotation. In this way, using one hand the surgeon can bring the assembly comprising the handling element with the medical instrument to the transfer station and connect the medical instrument to the sterilization-sensitive operating part, without having to grip the transfer station or respectively the sterilization-sensitive operating part.

In a further embodiment of the invention the docking and undocking mechanism comprises a first position, in which the handling element is locked on the transfer station and the sterilization-sensitive operating part and the medical instrument connected therewith are released for withdrawal.

The advantage of this measure is that not until the handling element is locked on the transfer station are the sterilization-sensitive operating part and the medical instrument released for withdrawal. This ensures that the operating part can only be withdrawn from the transfer station when the sterile hose arranged on the handling element is placed such that the sterilization-sensitive operating part is automatically sheathed with the sterile hose when withdrawn from the transfer station.

In a further embodiment of the invention the docking and undocking mechanism comprises a second position, in which the sterilization-sensitive operating part and the medical instrument connected therewith are released for returning.

The advantage of this measure is firstly that if the sterilization-sensitive operating part, which normally comprises a cable, is withdrawn too far by brief actuation of the handle (from the first position to the second position of the docking and undocking mechanism) the operating part with the cable is released for returning. Secondly, such a configuration of the docking and undocking mechanism enables the sterilization-sensitive operating part to be able to be guided back into the transfer station again on the completion of the work. The return of the sterilization-sensitive operating part to the transfer station can take place via a spring mechanism or via an electromotor.

In a further embodiment of the invention the docking and undocking mechanism comprises a third position, in which the connection between the medical instrument and the sterilization-sensitive operating part is disconnectable.

The advantage of this measure is that the medical instrument can be separated from the sterilization-sensitive operating part accommodated in the transfer station after use.

In a further embodiment of the invention the docking and undocking mechanism comprises a fourth position, in which the locking of the handling element is unlockable.

The advantage of this measure is that the handling element can be removed from the transfer station.

Further features and advantages will become apparent from the following description and the attached drawings.

It is understood that the abovementioned features and those still to be explained hereinbelow can be used not only in the given combination, but also in other combinations or on their own, without departing from the scope of the present invention.

BRIEF DESCRIPTION OF THE DRAWINGS

The invention will now be described and explained in greater detail by means of selected exemplary embodiments in connection with the attached drawings, in which.

DETAILED DESCRIPTION OF PREFERRED EMBODIMENTS

Figure 1:
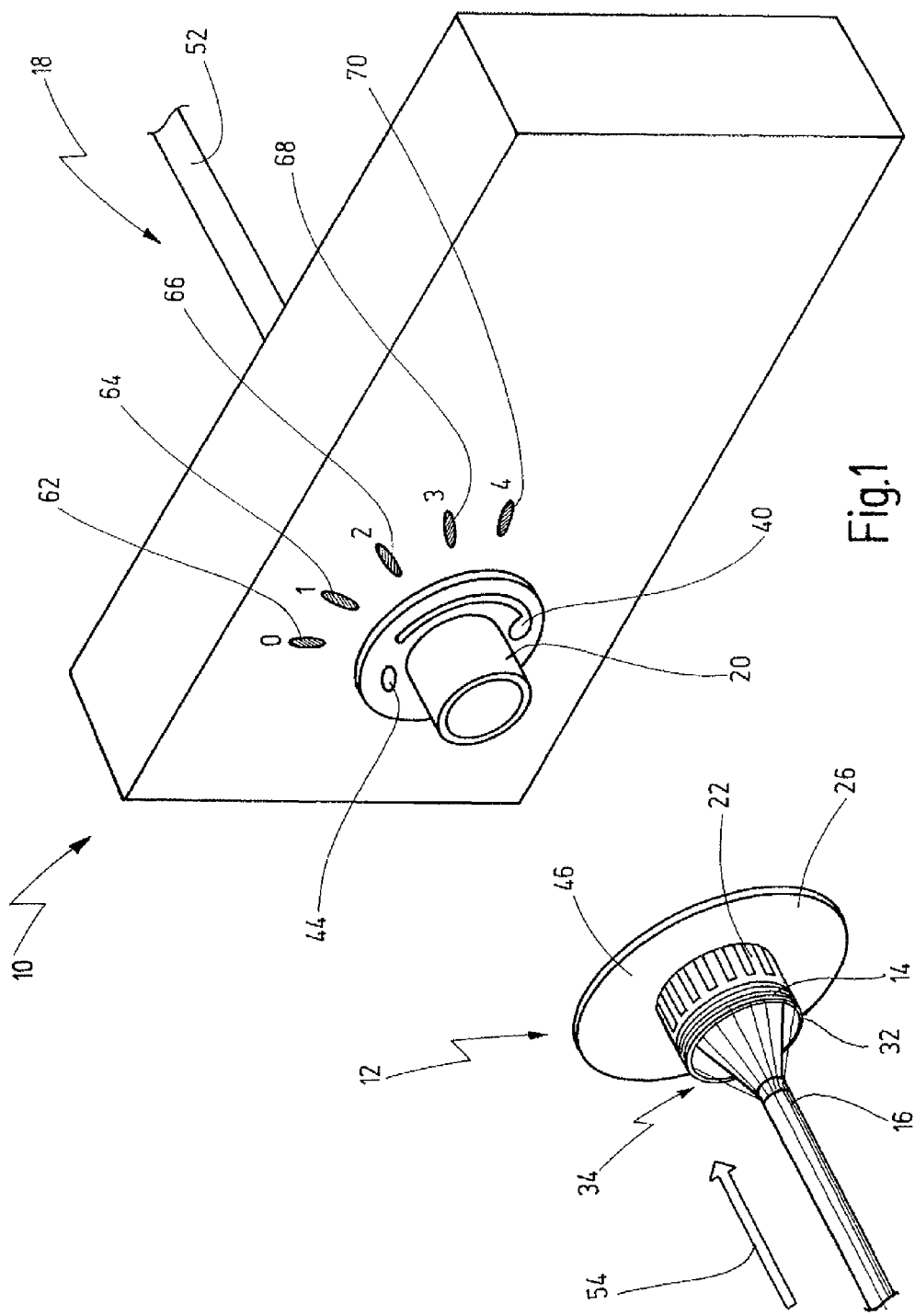
FIG. 1 is a perspective view of a device of the invention.

A device for the sterile sheathing of a sterilization-sensitive operating part illustrated in FIGS. 1 to 5 is designated in its entirety by reference numeral 10.

The device 10 illustrated in FIG. 1 has a handling element 12, which comprises a bundled sterile hose 14. Connected fixedly to the hose 14 is a medical instrument 16.

The device 10 further comprises a transfer station 18, in which a sterilization-sensitive operating part 20, here shown only fragmentarily, is accommodated.

Figure 2:
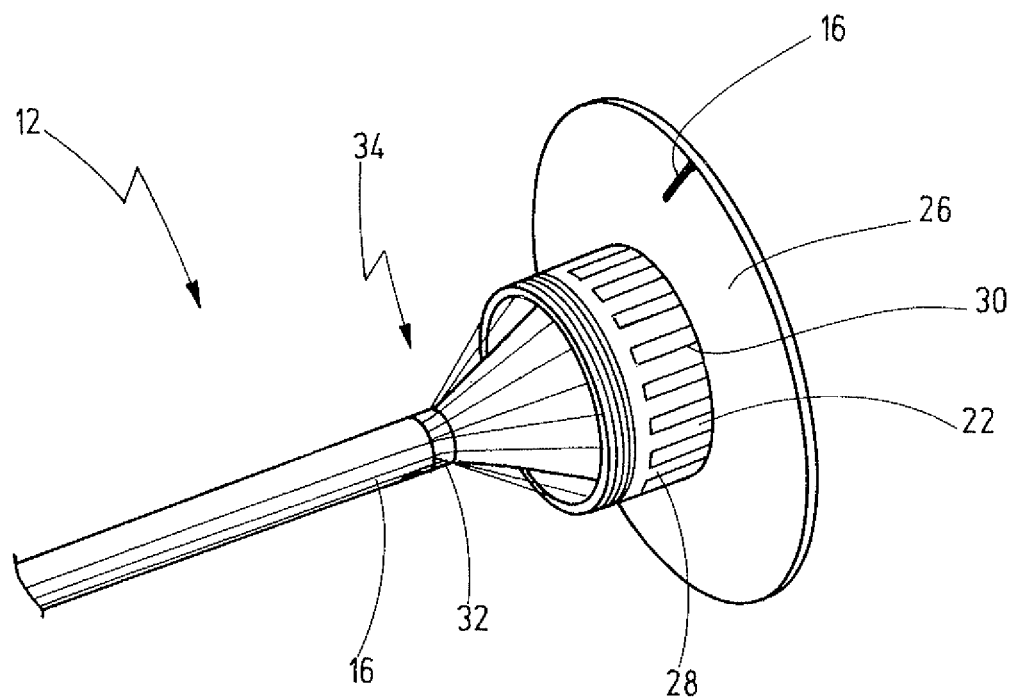
FIG. 2 is an enlarged perspective view of the distal area of a handling element connected to the medical instrument.

The handling element 12 on the distal side comprises a handle 22, as is evident in particular from the enlarged illustration in FIG. 2.

Figure 3:
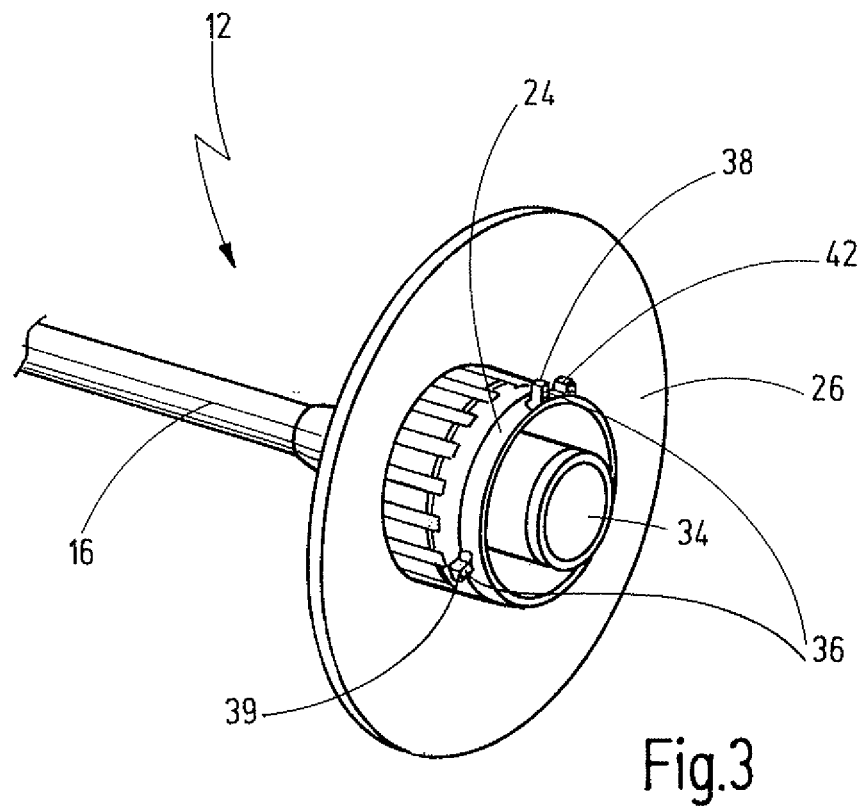
FIG. 3 is a perspective view of the proximal area of the handling element.

On the proximal side the handling element 12 comprises a coupling 24, which is evident from the illustration in FIG. 3. The handling element 12 is connected to the transfer station 18 by means of the coupling 24.

The handling element 12 also comprises a flat base part 26, from which the handle 22 and the coupling 24 protrude. In this exemplary embodiment the base part 26 is designed discoidal. The size of the base part 26 is selected such that when a hand is gripping the handle 22 it does not make contact with the transfer station 18 when coupling to it. This prevents any contamination from the non-sterile transfer station 18 reaching the handling element 12. This correspondingly prevents the doctor from being contaminated when grasping the handling element 12.

The handle 22 is designed as an annular flange 28, in the outside of which a notched pattern 30 is cut, so that the handle 22 can be gripped securely by fingers of a human hand.

Fixed on the handle 22 is a proximal end of the sterile hose 14. A distal end of the hose 14, shown in FIGS. 2 and 3 in a bundled form, is attached to the medical instrument 16. In this exemplary embodiment the distal end 32 of the hose 14 is fixed to a proximal end region 34 of the medical instrument 16. This fixing is done in this exemplary embodiment by glueing the hose 14 onto the medical instrument 16. The proximal end 34 of the medical instrument 16 is plugged into an opening in the base part 26 not evident here.

The proximally arranged coupling 24, which is evident from the illustration in FIG. 3, is designed in this exemplary embodiment as a bayonet coupling.

The coupling 24 designed as a bayonet coupling has a coupling element 36, which comprises pins 38, 39. Arranged on the transfer station 18 is a bayonet guide 40, as is evident in particular from the illustration in FIG. 1. When the handling element 12 is connected to the transfer station 18 the pins 38, 39 engage in the bayonet guide 40. Turning the handling element 12 locks it.

Figure 4:
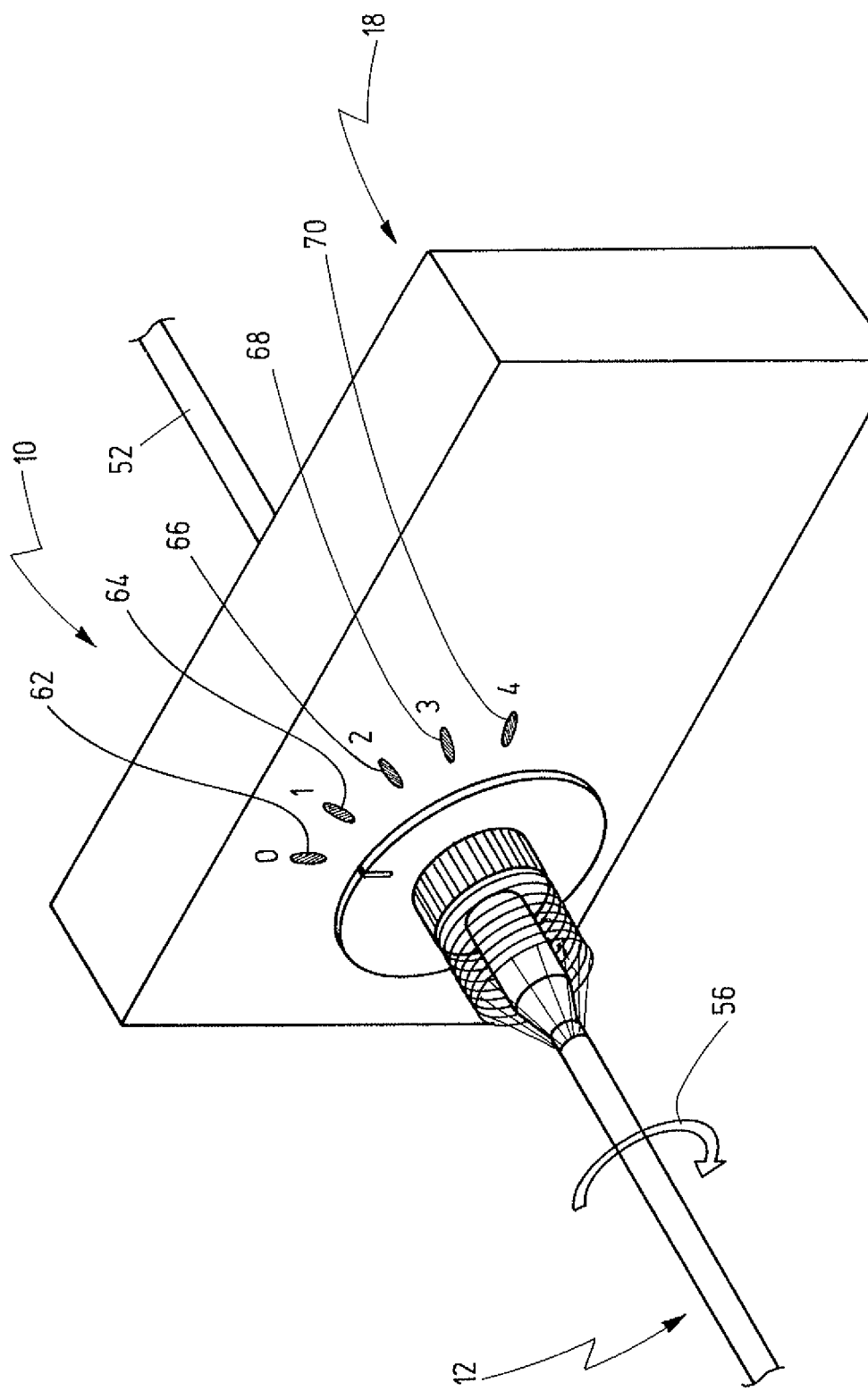
FIG. 4 illustrates a situation, in which the handling element is connected to the transfer station and the medical instrument is connected to the sterilization-sensitive operating part.
Figure 5:
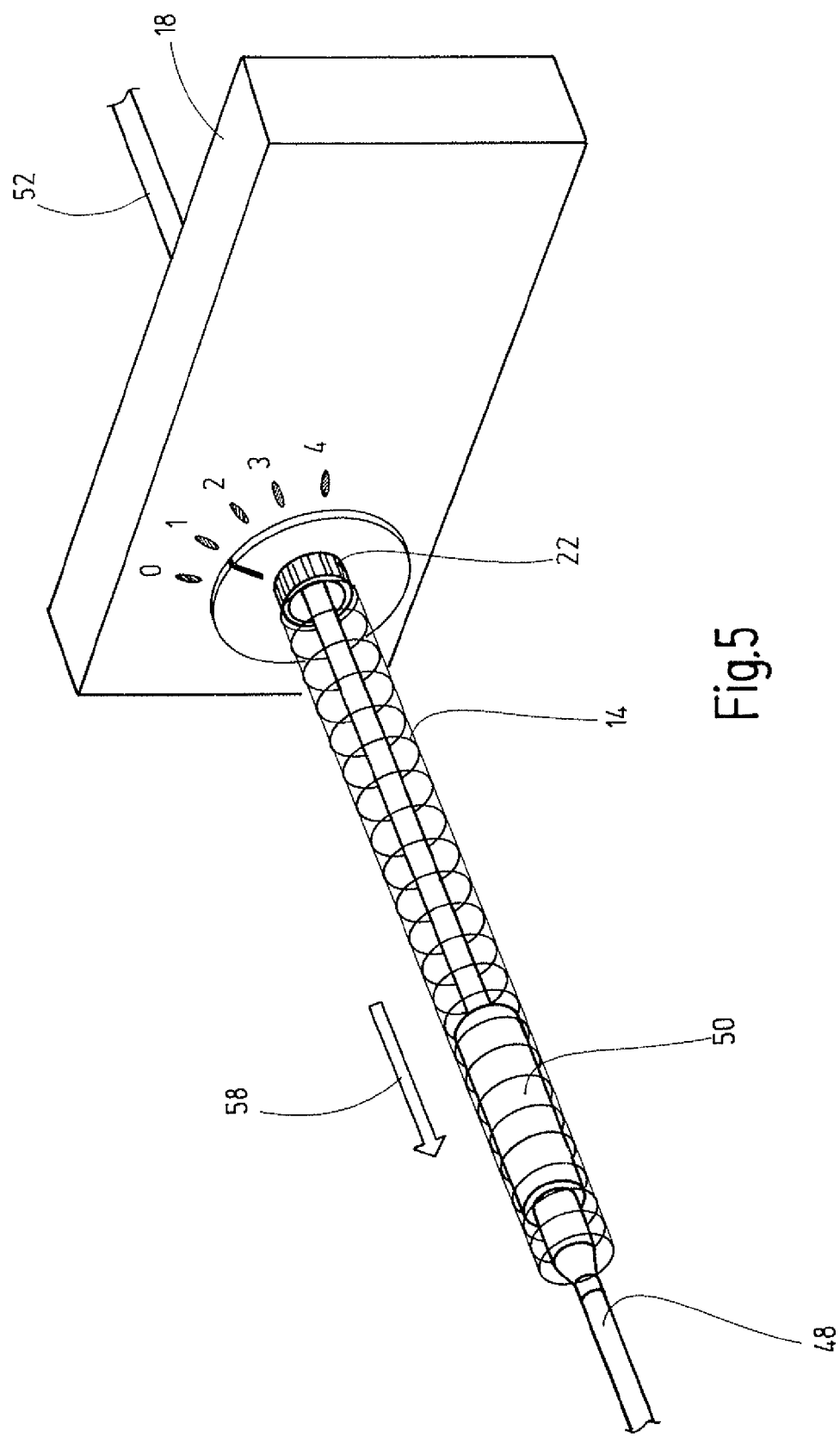
FIG. 5 is an illustration comparable to the illustration in FIG. 4, whereby the sterilization-sensitive operating part is removed from the transfer station and sheathed with the sterile hose.

The handling element 12 further comprises a control cam 42 arranged on the proximal side. When the handling element 12 is connected to the transfer station 18 the control cam 42 is connected to a contact switch 44, which is arranged on the transfer station 18. A docking and undocking mechanism 60, which is described in greater detail hereinbelow in connection with FIGS. 4 and 5, is thereby actuated.

Arranged on the base part 26 is an orientation feature 46, the function of which will be described in greater detail hereinbelow.

The medical instrument 16, which is connected fixedly to the distal end 32 of the hose 14 and in FIGS. 1 to 5 is illustrated only fragmentarily, is designed in this exemplary embodiment as endoscope 48. The endoscope 48 illustrated in this exemplary embodiment is designed as a disposable instrument.

The endoscope 48 designed as a disposable instrument comprises the following elements, not evident from any of the figures, specifically at least one video sensor with a lens arranged on the distal side, a light-transfer element, which guides light from proximal to distal, and an electric transfer system, which transmits the image information.

In this exemplary embodiment the proximal end 34 of the endoscope 48 is arranged such that it protrudes proximally over the coupling 24, as is evident in particular from the illustration in FIG. 3.

The sterilization-sensitive operating part 20 is designed in this exemplary embodiment as a handle 50, connected to a cable 52. The sterilization-sensitive operating part 20 contains sensitive electronic components and an integrated lighting unit with LEDs or respectively fibre optics, not illustrated here.

The operating part 20 is accommodated in the transfer station 18 such that its distal end protrudes in front of the transfer station 18, as is evident in particular from the illustration of FIG. 1.

The distal end of the operating part 20 is designed such that it is suitable for taking up the proximal 34 end of the medical instrument 16, so that the medical instrument 16 is coupled to the operating part 20.

The handling of the device 10 will be explained by means of FIGS. 4 and 5 in connection with FIG. 1.

The sterilization-sensitive operating part 20 is inserted in the transfer station 18 into the non-sterile area and locked against withdrawal, insertion and rotation. This situation is illustrated in FIG. 1.

An assembly comprising the handling element 12, the sterile hose 14 and the medical instrument 16 connected fixedly to the sterile hose 14 is removed by the surgeon from a sterile wrapping in the sterile area.

This compact unit is gripped on the handle 22 by a sterile hand of a person and the assembly is brought to the transfer station 18 (see arrow 54, FIG. 1).

The proximal end 34 of the medical instrument 16 is first inserted into the distal end of the operating part 20, which protrudes in front of the transfer station 18. This connects the medical instrument 16 to the operating part 20.

At the same time, the pins 38, 39 of the coupling 24 are inserted into the bayonet guide 40, which is arranged on the transfer station 18. This situation is illustrated in FIG. 4.

When the handling element 12 is attached to the transfer station 18 the handling element 12 is to be aligned such that the orientation feature 46 of the base part 26 is in alignment with a start position 62 of the docking and undocking mechanism 60.

These procedures can be completed with a single, sterile hand of one person.

Turning the handle 22 from the start position 62 to the first position 64 of the docking and undocking mechanism 60 locks the handling element 12 on the transfer station 18 by means of the bayonet coupling (see arrow 56, FIG. 1).

In the first position 64 the operating part 20 locked in the transfer station 18 is at the same time released for withdrawal.

In this position 64 the medical instrument 16, arranged in the sterile area, is gripped by the surgeon and withdrawn from the transfer station (see arrow 58, FIG. 5). The operating part 20 is thereby withdrawn from the transfer station 18. During the withdrawal the sterile hose 14 is automatically unfolds itself over the operating part 20 and the cable 48. This situation is illustrated in FIG. 5.

In the first position 64 of the docking and undocking mechanism 60, designated as a working position, the medical instrument 16 with the operating part 20 is now freely movable.

If the operating part 20 was withdrawn too far, the operating part 20 can be released for returning by brief actuation of the handle 22 from the first position 64 to a second position 66.

On completion of the surgical intervention the handling element 12 is brought to the second position 66 of the docking and undocking mechanism 60 by turning the handle 22. In the second position 66 of the docking and undocking mechanism 60 the operating part 20 and thus the handle 48 and the medical instrument 16 are pulled back, namely to the extent where the operating part 20 is locked in the transfer station 18. This pulling back is done by way of a spring mechanism or by way of an electromotor.

During the withdrawal the hose 14 folds itself up more or less before the handle 22.

The handling element 12 is then brought to a third position 68 of the docking and undocking mechanism 60 by turning the handle 22. In this position 68 the connection between the medical instrument 16 and the operating part 20 is disconnected, so that the medical instrument 16 is separated from the operating part 20.

The handling element 12 is then brought to a fourth position 70 of the docking and undocking mechanism 60 by turning the handle 22. In the fourth position 70 the handling element 12 is detached from the transfer station 18.

The assembly removed from the transfer station 18 comprising the handling element 12, the hose 14 and the medical instrument 16, which in this exemplary embodiment is designed as a disposable instrument, is disposed of without being cleaned.

This procedure also can be done with one hand.

When a reusable instrument is used, the handling of the device 10 is the same as for the disposable instrument, only with the difference that prior to being connected fixedly to the hose 14 the reusable instrument must be sterilized. On completion of work the reusable instrument is separated from the hose 14 and cleaned.

What is claimed is:

1. A device for the sterile sheathing of a sterilization-sensitive operating part, which can be connected to a medical instrument for a surgical intervention, said device comprising
    a handling element, having a distal end and a proximal end, comprising
        a bundled sterile hose having a distal end and a proximal end, the proximal end of said sterile hose being connected to said distal end of said handling element, and
        an opening, through which said sterilization-sensitive operating part can be inserted into said sterile hose from proximal to distal such, that said sterilization-sensitive operating part can thereby be sheathed with said sterile hose,
    a medical instrument having a distal end and a proximal end, connected fixedly at said proximal end to said distal end of said sterile hose, and
    a separate transfer station, wherein said sterilization-sensitive operating part is accommodated in said transfer station, said sterilization-sensitive operating part containing sterilization-sensitive electronic components, whereby said handling element can be releasably connected with its proximal end to said transfer station such that said proximal end of said medical instrument and a distal end of said sterilization-sensitive operating part can be connected to one another and whereby this assembly can be withdrawn from said transfer station, whereby said sterilization-sensitive operating part is automatically sheathed with said sterile hose when being withdrawn from the transfer station in a distal direction through said opening of said handling element.

2. The device of claim 1, wherein said handling element comprises a handle on the distal side.

3. The device of claim 1, wherein said handling element comprises a coupling on the proximal side.

4. The device of claim 2, wherein said handling element comprises a coupling on the proximal side.

5. The device of claim 4, wherein said handling element comprises a flat base part, from which said handle and said coupling protrude.

6. The device of claim 2, wherein said sterile hose is attached to the handle.

7. The device of claim 2, wherein said handle is designed as an annular flange.

8. The device of claim 3, wherein said coupling comprises a coupling element.

9. The device of claim 3, wherein said coupling is designed as a bayonet coupling.

10. The device of claim 5, wherein said base part comprises an orientation feature.

11. The device of claim 1, wherein said handling element and said hose are designed as disposable elements.

12. The device of claim 1, wherein said medical instrument is designed as a disposable instrument.

13. The device of claim 1, wherein said medical instrument is designed as a reusable instrument.

14. The device of claim 2, wherein said transfer station comprises a docking and undocking mechanism, which can be actuated via the handle.

15. The device of claim 14, wherein said transfer station comprises operational controls and wherein said docking and undocking mechanism can be actuated via said operational controls.

16. The device of claim 14, wherein said docking and undocking mechanism comprises a start position, in which said sterilization-sensitive operating part is locked in said transfer station.

17. The device of claim 14, wherein said docking and undocking mechanism comprises a first position, in which said handling element is locked on said transfer station and said sterilization-sensitive operating part and said medical instrument connected therewith are released for withdrawal from said transfer station.

18. The device of claim 14, wherein said docking and undocking mechanism comprises a second position, in which said sterilization-sensitive operating part and said medical instrument connected therewith are released for return to said transfer station.

19. The device of claim 14, wherein said docking and undocking mechanism comprises a third position, in which a connection between said medical instrument and said sterilization-sensitive operating part is disconnectable.

20. The device of claim 14, wherein said docking and undocking mechanism comprises a fourth position, in which a locking of the handling element with said transfer station is unlockable.

\* \* \* \* \*